United States Patent [19]
McVey et al.

[11] Patent Number: 4,824,473
[45] Date of Patent: * Apr. 25, 1989

[54] TREATMENT OF PLANTS WITH A COMBINATION FERTILIZER COMPOSITION

[75] Inventors: George R. McVey; Kenneth W. Tornberg; Larry R. Widell; George E. Wood, all of Marysville, Ohio

[73] Assignee: The O.M. Scott & Sons Company, Marysville, Ohio

[*] Notice: The portion of the term of this patent subsequent to Nov. 3, 2004 has been disclaimed.

[21] Appl. No.: 863,174

[22] Filed: May 14, 1986

Related U.S. Application Data

[63] Continuation-in-part of Ser. No. 596,006, Apr. 2, 1984, Pat. No. 4,704,160.

[51] Int. Cl.$^4$ ...................... A01N 43/64; A01N 43/60
[52] U.S. Cl. ............................................. 71/92; 71/76
[58] Field of Search ....................................... 71/76, 92

[56] References Cited

U.S. PATENT DOCUMENTS

| 3,462,057 | 8/1969 | McVey et al. | 71/76 |
| 4,002,608 | 1/1977 | Benefiei et al. | 260/251 |
| 4,013,444 | 3/1977 | Fridinger | 71/76 |
| 4,043,405 | 1/1981 | Brilasubramadyan | 71/76 |

Primary Examiner—Catherine L. Mills

[57] ABSTRACT

Vegetation comprising herbaceous and woody ornamental plants and vegetable crops are treated by applying to the vegetation a nitrogen containing fertilizer and from 0.006 to 6.0 pounds per acre of a plant growth regulator. The plant growth regulator is one which regulates the growth of the vegetation by retardation of gibberellin synthesis. The ratio by weight of nitrogen in the fertilizer to the plant growth regulator is at least forty to one.

30 Claims, No Drawings

TREATMENT OF PLANTS WITH A COMBINATION FERTILIZER COMPOSITION

This application is a continuation-in-part of our copending application Ser. No. 596,006, filed Apr. 2, 1984, now U.S. Pat. No. 4,704,160.

This invention relates to a process for the treatment of herbaceous and woody ornamental plants and vegetable crops with a combination fertilizer composition and to the combination fertilizer composition so used.

Compounds which accelerate or retard the rate of growth of plants have been known for some time. Chemicals which retard or inhibit shoot and leaf elongation can be categorized by four modes of action: (1) inhibition of mitosis in the meristematic tissue which stops cell division and cell elongation (mitotic inhibitors), (2) reduction of cell elongation by inhibiting or retarding gibberellin synthesis, a plant hormone necessary for cell elongation (gibberellin synthesis inhibitors), (3) regulating auxin activity and transport (auxin modifiers) and (4) killing terminal buds thus reducing apical dominance (chemical bud pinchers). Mitotic inhibitors include such compounds as chlorflurenol, mefluidide, and maleic hydrazide. These compounds and their use as growth regulators are further discussed in "Plant Growth Regulating Chemicals", Louis G. Nickell, CRC Press, Vol. II (1983). Those which retard gibberellin synthesis include such compounds as paclobutrazol (PP-333) and flurprimidol (EL-500), discussed further below.

The combination of a plant growth regulator of the type which inhibits mitosis and a fertilizer was first reported in 1969 in McVey et al U.S. Pat. No. 3,462,257. The stated purpose of the combination was to improve turf color and quality while reducing turf growth. However, the combination product disclosed in the McVey et al patent possesses a number of limitations which have effectively prevented its use. The plant growth regulator disclosed in the McVey et al patent, 6 azauracil and certain of its derivatives and salts, requires a usage level well above the level of tolerance of certain grass species. Moreover, recovery from inhibition with this combination product is rapid, resulting in surge growth and narrower blade widths, both undesirable in turf maintenance programs.

The compounds paclobutrazol [(2RS, 3RS)-1-(4 chlorophenyl)-4, 4-dimethyl-2-(1,2,4-triazol-1-yl)pentan-3-ol] and flurprimidol [α-(1-methylethyl)-α[4-(trifluoromethoxy)phenyl]-5-pyrimidine-methanol] have been reported relatively recently as plant growth regulators. Paclobutrazol and its use as a fungicide and plant growth regulator are disclosed in U.S. Pat. No. 4,243,405 which issued on Jan. 6, 1981. Flurprimidol and its use as a herbicide, fungicide, and plant growth regulator are disclosed in U.S. Pat. No. 4,002,628 which issued on Jan. 11, 1977. Ancymidol is the commonn name for the chemical a-cyclopropyl-a-(p-methoxyphenyl)-5-pyrimidimethanol.

Our aforementioned copending parent application Ser. No. 596,006, now U.S. Pat. No. 4,704,160, discloses a combination fertilizer composition in which the effect of a fertilizer component in combination with certain plant growth regulators is considerably enhanced over the use of the fertilizer alone, particularly in extending the period of the fertilizer's desirable response and reducing the amount of fertilizer necessary to maintain quality vegetation. That application discloses the use of the combination fertilizer product on turf grasses. The present application deals with the use of a similar fertilizer-plant growth regulator combination product on herbaceous and woody ornamental plants and vegetable crops. It has been found the combination fertilizer composition of the invention enhances foliage color and plant quality and increases flower production as compared with the use of similar or even greater amounts of the fertilizer alone.

The present invention is accordingly directed to a process for treating vegetation comprising herbaceous and woody ornamental plants and vegetable crops comprising applying to the vegetation a nitrogen containing fertilizer and from 0.006 to 6.0 pounds per acre of a plant growth regulator, said plant growth regulator being a compound which regulates the growth of said vegetation by retardation of gibberellin synthesis, the ratio by weight of nitrogen in said fertilizer to said plant growth regulator being at least forty to one, said fertilizer and plant growth regulator being applied in a proportion which is effective to improve the quality of the vegetation, the improvement in quality being both greater and extending for a longer period than that resulting from the application of the fertilizer or plant growth regulator alone. The composition of the invention is a composition for treating herbaceous and woody ornamental plants and vegetable crops comprising a nitrogen containing fertilizer and from 0.006 to 6.0 pounds per acre of a plant growth regulator, said amount being based on an amount of the composition for treating one acre of said vegetation, said plant growth regulator being a compound which regulates the growth of said vegetation by retardation of gibberellin synthesis, the ratio by weight of nitrogen in said fertilizer to said plant growth regulator being at least forty to one, said fertilizer and plant growth regulator being present in said composition in proportions which is effective to improve the quality of the vegetation, the improvement in quality being both greater and extending for a longer period than that resulting from the application of the fertilizer or plant growth regulator alone.

For herbaceous ornamental plants and vegetable crops, the ratio by weight of nitrogen in the fertilizer to the plant growth regulator will normally be at least one hundred to one. In many instances, this ratio will run to as high as 45,000 to one. For woody ornamental plants, this ratio may run as low as forty to one, but preferably no less than 70 to one, and as high as 25,000 to one. The amount of plant growth for herbaceous ornamental plants and vegetable crops will normally be from 0.006 to 0.74 pounds per acre. The amount of plant growth regulator for woody ornamental plants will normally run from 0.060 to 6.0 pounds per acre. The reason for the much higher upper limit for woody ornamental plants is that media containing bark reduce the biological activity of plant growth regulators. Most growers of woody ornamental plants use such bark-contining media.

Many of the advantages of the combination fertilizer composition of the invention, as well as its manner of use, are set forth in detail in our aforesaid parent application Ser. No. 596,006, the disclosure of which is hereby incorporated by reference. For herbaceous and woody ornamental plants and vegetable crops, there are, however, certain additional advantages specific to these types of vegetation. As in the case of turf grasses, the effect of the fertilizer is enhanced with the addition of the plant growth regulator, the period of desirable response of the fertilizer is extended, and the amount of fertilizer necessary to maintain quality vegetation is reduced. In addition, the combination compositions of the invention produce a higher quality, more compact plant, and an increase in flower production.

The fertilizers, when used in the proportions herein set forth, tend to act as antidotes for the otherwise injurious action of the plant growth regulator on plants. Furthermore, the nitrogen/plant growth regulator ratios herein set forth provide biological activity at extremely low rates of the plant growth regulator as a result of synergism between these two components. Moreover, by using small proportions of the growth regulator, either simultaneously with or while the plant is actively growing as a result of the application of the nitrogen fertilizer, injury to the vegetation is eliminated. The fertilizer should be applied simultaneously with application of the regulator, and in any event, before the growth regulator damages the plant. Reference herein to application of the fertilizer and growth regulator in combination is intended to encompass the application of the materials in either of these fashions, that is, either simultaneously which is preferable, or within a relatively short period of time after the application of the fertilizer or the growth regulator. The time period will vary with the type and amount of fertilizer and growth regulator but should normally be no longer than a week if the growth regulator is applied first and no longer than a month if the fertilizer is applied first.

It has been found that there is less criticality in the method and rate of application of the combined fertilizer and growth regulator than there is with the growth regulator alone. That is, the invention makes possible a wide margin of safety between desirable plant response and objectionable phytotoxicity. Moreover, repeat applications may be carried out without danger of an adverse effect on the plant. Most known plant growth regulators, particularly mitotic inhibitors, are in fact herbicides at higher application rates and when used even at low application rates have a phytotoxic potential. The invention involves using only those plant growth regulators which operate by retardation of gibberellin synthesis and only at extremely low rates, sufficient to obtain biological response and yet have an adequate margin of safety. The invention also involves using very high proportions of nitrogen to mitigate any phytotoxic effect, even at multiples of normal nitrogen application rates. The advantsages of the invention are particularly unexpected in view of the previous sensitivity of plants to the level of application of plant growth regulators. In addition, the invention has been found to be effective on a broad variety of plant species and over a wide geographical area.

The term "plant growth regulator" as used herein means a substance intended, through physiological action, to retard the rate of growth or rate of maturation, or otherwise alter the behavior of plants. A more complete discussion of plant growth regulators is contained in the aforesaid text "Plant Growth Regulating Chemicals", by Louis G. Nickell. Those growth regulators included within the scope of the invention whose mode of action effects gibberellin synthesis are defined in the literature as inhibitors of gibberellin synthesis. However, the growth regulating compounds are used in the present invention in formulations and at rates which retard rather than stop or suppress the growth of vegetation. Accordingly, the compounds which affect gibberellin synthesis are referred to herein as those which retard gibberellin synthesis.

Herbaceous ornamentals include such flowers as geraniums, petunias, and marigolds. Woody ornamentals include such plants as Euonymus, Juniper, Thuja and Buxus. Vegetable crops require no definition but are here illustrated by tomatos, cucumbers, and lettuce.

The following examples illustrate the practice of the invention. Unless otherwise indicated, all parts and percentages are by weight. Also, unless otehwise indicated, reference in the examples to application rates indicates weight of nitrogen, in the case of fertilizers, and weight of active ingredient, in the case of plant growth regulators, applied to one acre of vegetation. The various measurements and tests carried out on the vegetation were conducted as follows:

Foliage Color: The intensity of green was estimated using a scale of 10 to 1 with 10 being a very excellent dark green color. Acceptable foliage color ranges from 7-10.

Plant Quality: Plant quality was rated on a scale of 1 to 10 with 1 being a very excellent quality. Quality was based on color, uniformity of growth, density and texture (uniformity of leaf size). A rating of 1-3 is considered excellent with acceptable quality ranging up to 6.

Plant Height: The plant was measured to the average height of the new growth in greenhouse tests. Under field conditions, the height was taken from the soil surface to the average height of the new leaves.

Foliage Fresh Weight: The plants were cut at ground level and the fresh weight of the plant determined.

EXAMPLE 1

Mustang Geranium seedlings were planted in synthetic potting media containing all essential elements with methylene urea nitrogen ranging from zero to 348 lbs. N/acre in increments of 87 lbs. applied August 21. The nitrogen source was methylene urea (36% cold water insoluble nitrogen). The plants were grown in 1 gallon containers and treated with 125 ml of water containing 0.0, 0.10, 0.20., and 0.40 parts per million (ppm) of PP-333 (0.0, 0.06, 0.12, and 0.24 lbs. per acre) on September 12. Results were observed 62 days after treatment.

Foliage color and plant quality increased with the first increment of PP-333 (0.06 lbs./acre) at all rates of nitrogen (87-348 lbs//acre). However, at higher rates of PP-333, foliage color and plant quality only improved if higher rates of nitrogen were used (174-348 lbs. N/acre). At the lower rates of N (0-87 lbs./acre) plant color decreased or remained the same when combined with the higher rate of PP-333 (0.12 and 0.24 lb./acre). Plant height was reduced only in the presence of adequate nitrogen (174-348 lbs. N/acre) and PP-333 (0.24 lbs./acre for 174 and 261 lbs. N/acre and 0.06 lbs./acre for 348 lbs. N/acre). Plant fresh weight followed similar trend but only at the highest rate of nitrogen. This example demonstrates that the higher the level of nitrogen applied, the lower the rate of PP-333 needed to realize a growth regulatory affect on plant height and fresh weight. The N/PGR ratio ranged from 348/0.06 (5800) to 261/0.24 (1088) to 174/0.24 (725).

At the termination of the study, dry weights were recorded. The results support the conclusion that PP-333 has little impact on growth (dry wt) until the nitrogen level is adequate (261-348 lbs. N/acre). Foliage color, plant quality and milligrams of nitrogen removed in the tissue also following a similar trend. Total blossom production, in contrast, is increased more dramatically at the lower nitrogen level in the presence of PP-333 as compared to nitrogen only.

The response of geraniums to fertilizer and PP-333 is shown below in Table I. In this csse, the data was subjected to analysis to determine if PP-333 and nitrogen were synergistic. Values presented are based on percent of the control which received no fertilizer or PP-333. The test for synergism is obtained by using the percent of control values as set forth in:

Colby, S. R. (1966) Calculating Synergistic & Antagonistic Response of Herbicide Combinations, Weeds, Vol. 15, p. 20–22.

$$\frac{\text{Fertilizer} \times PGR}{100^{n-1}} \quad (n = \text{number of chemicals})$$

For color the values would be:

$(113 \times 92)/100 = 103$

Any value greater than 103 would constitute synergism.

Table I accordingly shows the response of mustang geraniums to fertilizer and PP-333 applied separately and in combination. As indicated above, the numerical values, except of course, for milligrams of N removed, are percentage of a control plant which received neither fertilizer or PP-333. Total flowers were the total over a 110 day growing period.

with an associated synergistic reduction in plant height, weight and milligrams of nitrogen removed in the tissue. This combination has resulted in a high-quality compact plant with an increase in flower production using less than half the nitrogen used by plant fertilizer with only nitrogen.

EXAMPLE 2–4

Mustang geranium seedlings in the 3–5 leaf stage were transplanted to 1 gallon cans containing a synthetic soil known by the trademark Metro-Mix 200. Metro-Mix 200 contains milled Canadian sphagnum peat moss, No. 3 grade horticultural vermiculite, wetting agent, a small nutrient charge, coarse horticultural perlite and selected washed granite sand. The seedlings were fertilized with a Scott Starter fertilizer having an 18-24-6 N—$P_2O_5$—$K_2O$ analysis with urea, methylene urea, monoamoninum phosphate, and potassium chloride used as the nutrient sources on a vermiculite carrier. Eighty seven or 261 lbs. of N/acre were used two weeks after transplanting (June 4). On June 11, various rates of PP-333, El-500 and Ancymidol (0, 0.03 and 0.15 lbs acre) were applied as a soil drench using 125 ml/pot at 0.0, 0.5, and 2.5 ppm of the PGR. After two months, various observations were recorded and are shown in Tables II, III, and IV.

TABLE II

| Sample Number | Formulation | N lbs/acre | PP-333 lbs/acre | Plant Ht. (cms) | Plant Color (10 > 1) | Plant Qual (1 > 10) | Fr. Wt. (gms) | Total Flower Count (No.) | Total Flower Wt. (gms) | Leaf Analysis N (%) | Leaf Analysis N in tissue (mgms) |
|---|---|---|---|---|---|---|---|---|---|---|---|
| 1 | Fertilizer | 87 | 0 | 28 | 5.0 | 5.0 | 110 | 9.0 | 45 | 1.77 | 390 |
| 2 | Fertilizer & PGR | 87 | .03 | 15 | 9.8 | 3.5 | 88 | 10.5 | 43 | 2.76 | 500 |
| 3 | Fertilizer & PGR | 87 | .15 | 12 | 10.0 | 4.0 | 69 | 10.0 | 38 | 3.31 | 460 |
| 4 | Fertilizer | 261 | 0 | 30 | 7.5 | 2.8 | 173 | 11.1 | 57 | 2.40 | 840 |

TABLE III

| Sample No. | Formulation | N lbs/acre | EL-500 lbs/acre | Plant Ht. (cms) | Plant Color (10 > 1) | Plant Qual. (1 > 10) | Fr. Wt. (gms) | Total Flower Count (No.) | Total Flower Wt. (gms) | Leaf Analysis N (%) | Leaf Analysis N in tissue (mgms) |
|---|---|---|---|---|---|---|---|---|---|---|---|
| 1 | Fertilizer | 87 | 0 | 28 | 5.0 | 5.0 | 110 | 9.0 | 45 | 1.77 | 390 |
| 2 | Fertilizer & PGR | 87 | .03 | 19 | 9.0 | 3.0 | 122 | 11.8 | 55 | 2.46 | 590 |
| 3 | Fertilizer & PGR | 87 | .15 | 12 | 10.0 | 4.5 | 64 | 9.5 | 36 | 3.00 | 390 |
| 4 | Fertilizer | 261 | 0 | 30 | 7.5 | 2.8 | 173 | 11.1 | 57 | 2.40 | 840 |

TABLE IV

| Sample No. | Formulation | ANCYMIDOL lbs./acre | Plant Ht. (cms) | Plant Color (10 > 1) | Plant Qual. (1 > 10) | Fr. Wt. (gms) | Total Flower Count (No.) | Total Flower Wt. (gms) | Leaf Analysis N (%) | Leaf Analysis N in tissue (mgms) |
|---|---|---|---|---|---|---|---|---|---|---|
| 1 | Fertilizer | 87 0 | 28 | 5.0 | 5.0 | 110 | 9.0 | 45 | 1.77 | 390 |
| 2 | Fertilizer & PGR | 87 .03 | 31 | 6.3 | 4.3 | 215 | 8.5 | 40 | 2.06 | 880 |
| 3 | Fertilizer & PGR | 87 .15 | 27 | 7.3 | 3.5 | 173 | 8.4 | 40 | 1.96 | 690 |
| 4 | Fertilizer | 261 0 | 30 | 7.5 | 2.8 | 173 | 11.1 | 57 | 2.40 | 840 |

As shown in Tables II–IV, plants treated with 87 lbs. N and PP-333 were more compact (shorter) with better or equal quality and better color than plants fertilized

TABLE I

| Sample No | Formulation | N lbs.acre | PP-333 lbs.acre | Color | Quality | Height | Total Flowers Percent of Control | Fresh Weight | Milligrams of N Removed |
|---|---|---|---|---|---|---|---|---|---|
| 1 | Fertilizer | 87 | 0 | 113 | 171 | 190 | 300 | 529 | 2770 |
| 2 | Plant Growth Reg | 0 | .24 | 92 | 89 | 96 | 100 | 114 | 100 |
| 3 | Fert and PGR | 87 | .24 | 184* | 232* | 174* | 992* | 442* | 1200* |

*Synergistic response

As shown in Table I, the combination of fertilizer and PGR resulted in a synergistic increase in plant color, quality, flower production, and nitrogen in the tissue with equal or three times more nitrogen. Flower count was equal or slightly increased as compared to plants fertilized with the low rate of nitrogen. The percent nitrogen in the leaf tissue as a result of PP-333 treatment in combination with the low rate of N was greater than plants receiving nitrogen at a triple rate without PP-333 (261 lbs. N/acre). Plant color, quality, flower count and tissue N is equal or superior to plants fertilized with 261 lbs. N/acre when 87 lbs. N/acre is combined with 0.03 lbs. PP-333/acre. The total N removed in the leaf tissue was reduced by 40-45 percent irrespectively of medium, resulting in improved nitrogen efficiency.

When plants were treated with EL-500, the results were every similar to those described above, however, higher rates were required to realize equal performance. Ancymidol, another GA synthesis retardant, was less effective than the above formulations. However, increasing rates of Ancymidol plus fertilizer increased color, quality and fresh weight with little effect on flowering. A rate adjustment should be made with each GA synthesis retardant to produce maximum results.

EXAMPLE 5

Petunia Lyric seedlings in the 2–4 leaf stage were transplanted into Metro-Mix 200 synthetic soil and fertilized with Scott Starter fertilizer (18-24-6) at 87 or 261 lbs. N/acre on May 22. On May 30, PP-333 was applied as a liquid drench using 125 ml of water containing 0, 0.1, 1.0, and 10.0 ppm at of PP-333 (0, 0.006, 0.06 0.6 lbs/acre.) On July 16, the plants were harvested and a number of observations recorded. These are set forth in Table V.

thetically was very pleasing, however, flower production was decreased suggesting that this rate is the upper limit.

At the higher rate of N (261 lbs./acre) and the lowest rate of PP-333 (0.006 lbs./acre) the plant is more responsive to the PGR then at the lower ratte of nitrogen (87 lbs./acre).

EXAMPLE 6

Marigold Cracker Jack seedlings in the 2–4 leaf stage were transplanted into Metro-Mix 200 and fertilized with Scott Starter fertilizer (18-24-6) at 87 or 261 lbs. N/acre on May 22. On May 30, PP-333 was applied as a liquid drench using 125 ml of water containing 0, 0.1, 1.0, and 10.0 ppm of PP-333 (0, 0.006, 0.06, and 0.6 lbs./acre.) On July 16, the plants were harvested and a number of observations recorded.

TABLE VI

| Sample | Formulation | N lbs/acre | PP-333 lbs/acre | Ht. (cms) | Width (cms) | Color (10 > 1) | Quality (1 > 10) | Fr. Wt (gms) | Flower Count (No) |
|---|---|---|---|---|---|---|---|---|---|
| 1 | Fertilizer | 87 | 0 | 59 | 43 | 6.3 | 3.7 | 142 | 1.7 |
| 2 | Fertilizer & PGR | 87 | .006 | 69 | 37 | 6.7 | 3.7 | 133 | 1.3 |
| 3 | Fertilizer & PGR | 87 | .06 | 58 | 35 | 6.3 | 3.3 | 144 | 1.0 |
| 4 | Fertilizer & PGR | 87 | .6 | 55 | 33 | 9.7 | 3.0 | 121 | 2.0 |
| 5 | Fertilizer | 261 | 0 | 69 | 36 | 7.0 | 1.7 | 175 | 1.3 |
| 6 | Fertilizer & PGR | 261 | .006 | 68 | 44 | 8.0 | 1.7 | 179 | 1.7 |
| 7 | Fertilizer & PGR | 261 | .06 | 65 | 44 | 9.3 | 1.7 | 160 | 1.7 |
| 8 | Fertilizer & PGR | 261 | .6 | 51 | 38 | 9.0 | 1.3 | 141 | 2.0 |

As shown in the above table, increasing the rate of PP-333 improved plant color (darker green foliage) and quality with an increase in flower number and a slight reduction in plant size (weight, width, and height). These differences were more dramatic at the higher fertility level (261 lbs. N/acre) (fresh weight, flower count, and plant quality).

EXAMPLE 7

First Lady Marigold seeds were sown on January 26 in Redi-Earth potting media contained in cell packs (72 cells/1.1 sq. feet, 50 cc/cell). Starter fertilizer was incorporated in all flats at a rate of 16 lbs N/acre as

TABLE V

| Sample | Formulation | N lbs/acre | PP-333 lbs/acre | Ht. (cms) | Width (cms) | Plant Color (10 > 1) | Quality (1 > 10) | F.W. (gms) | Flower (Count) No. | Leaf Tissue Analysis (% N) |
|---|---|---|---|---|---|---|---|---|---|---|
| 1 | Fertilizer | 87 | 0 | 39 | 65 | 6.0 | 4.3 | 114 | 20 | 3.34 |
| 2 | Fertilizer & PGR | 87 | .006 | 38 | 51 | 7.7 | 3.0 | 129 | 23 | 3.24 |
| 3 | Fertilizer & PGR | 87 | .06 | 35 | 42 | 8.0 | 3.3 | 96 | 26 | 4.06 |
| 4 | Fertilizer & PGR | 87 | .6 | 30 | 31 | 9.3 | 3.3 | 73 | 14 | 4.48 |
| 5 | Fertilizer | 261 | 0 | 40 | 51 | 7.3 | 2.7 | 141 | 37 | 3.90 |
| 6 | Fertilizer & PGR | 261 | .006 | 49 | 55 | 9.0 | 1.0 | 197 | 33 | 4.56 |
| 7 | Fertilizer & PGR | 261 | .06 | 32 | 41 | 9.0 | 2.7 | 139 | 28 | 3.50 |
| 8 | Fertilizer & PGR | 261 | .6 | 25 | 36 | 9.0 | 3.0 | 109 | 17 | 4.34 |

In contrast to other genera studied, extremely low rates of PP-333 (0.006 acre) increased plant fresh weight of Petunia Lyric. These differences were more dramatic at the higher rate of nitrogen. This was associated with an improvement in plant color and quality. Flower count was increased or decreased slightly at the low and high nitrogen level, respectively. At higher rates of PP-333, the typical inhibition of vegetative growth occurred with an associated increase in plant color. At the highest rate of PP-333 (0.6 lbs. acre) the plant aes- 18-24-6 to assure adequate growth. On February 27 when the plants were in the 2nd true leaf stage they were treated with zero or 96 lbs. N/acre as 18-24-6 and zero or 0.74 lbs. of PP-333 as a liquid drench. On the 17th day after treating height, color, quality, and fresh weights were recorded.

The potting media is known by the trademark Redi-Earth and contains milled Canadian sphagnum peatmoss, No. 3 grade horticultural vermiculite, a wetting agent and a small nutrient charge.

TABLE VII

| Sample No. | Formulation | N (lbs./acre) | PP-333 | Height | Color | Quality | Fresh Weight |
|---|---|---|---|---|---|---|---|
| | | | | | Percent of Control | | |
| 1 | Fertilizer | 96 | 0 | 125 | 181 | 167 | 148 |
| 2 | PGR | 0 | 0.74 | 87 | 76 | 98 | 87 |
| 3 | Fert. plus PGR | 96 | 0.74 | 108* | 257* | 208* | 131 |

*Synergistic response

As shown in Table VII, the combination of fertilizer and PGR resulted in a shorter, dark green plant with higher quality than when treated with fertilizers alone. The addition of the PGR alone induced poorer color, quality, and fresh weight than the control which received no fertilizer or PGR.

In the following Examples 8-13, several different vegetable crops were treated with various rates of a plant growth regulator in the presence of no, low, or high rates of fertilizer. Plant height, foliage color, plant quality, plant fresh weight, flower count, leaf tissue nitrogen, and fruit weight were recorded where applicable.

EXAMPLE 8

Beefmaster tomato seedlings in the 2-4 leaf stage were transplanted into Metro-Mix 200 and fertilized with Starter fertilizer at 87 or 261 lbs. N/acre on May 22. On May 30, PP-333 was applied as a liquid drench using 125 ml. of water containing 0. 0.1, 1.0, and 10.0 ppm of PP-333 (0, 0.006, 0.06 0.6 lbs/acre). On July 16, the plants were harvested and a number of observations recorded. The results are set forth in table VIII. All test results were taken the 48th day of the test except for flower count and leaf tissue analysis which were taken on the 27th day.

TABLE VIII

| Sample | Formulation | N lbs/acre | PP-333 | Ht. (cms) | Color (10 > 1) | Quality (1 > 10) | Stem F.W. (gms) | Flower Count (No) | Fruit Wt. (gms) | Leaf Tissue Analysis (N %) |
|---|---|---|---|---|---|---|---|---|---|---|
| 1 | Fertilizer | 87 | 0 | 127 | 2.5 | 6.5 | 250 | 33 | 82 | 1.49 |
| 2 | Fertilizer & PGR | 87 | .006 | 108 | 2.5 | 7.0 | 256 | 35 | 85 | 1.60 |
| 3 | Fertilizer & PGR | 87 | .06 | 94 | 5.5 | 4.5 | 227 | 37 | 79 | 1.77 |
| 4 | Fertilizer & PGR | 87 | .6 | 86 | 6.0 | 4.0 | 275 | 36 | 21 | 2.15 |
| 5 | Fertilizer | 261 | 0 | 129 | 2.0 | 6.0 | 318 | 32 | 227 | 1.77 |
| 6 | Fertilizer & PGR | 261 | .006 | 126 | 3.0 | 7.0 | 334 | 45 | 258 | 2.16 |
| 7 | Fertilizer & PGR | 261 | .06 | 98 | 6.0 | 4.5 | 330 | 54 | 188 | 2.59 |
| 8 | Fertilizer & PGR | 261 | .6 | 87 | 7.0 | 3.5 | 369 | 43 | 11 | 2.87 |

As shown in Table VIII, the addition of PP-333 to fertilized plants (87 and 261 lbs N/acre) improved plant color, quality, reduced plant height, increased stem weight and flower count (at high N rate only) and increased percent N in the leaf tissue. The fruit weight was only dramatically decreased at the highest rate of PP-333 (0.6 lb/acre). It is of interest that at the lowest rate of PP-333, the percent nitrogen in the leaf tissue, flower count, fruit weight, and stem weight, were increased with only a slight reduction in plant height. Quality and color of the leaves were very similar to plants receiving fertilizer only. The combination of fertilizer and PGR resulted in a shorter, more compact plant with improved leaf color and plant quality with an associated increase in plant weight, flower number, and percent nitrogen in the tissue. Fruit weight increased at the lowest rate of PP-333. The desirable responses realized were more dramatic at the higher nitrogen level. (Color, fresh weight, flower count, fruit weight, and % N in the tissue).

EXAMPLE 9

Big Girl Tomato seeds were sown on December 9 in Redi-Earth potting media contained in cell packs (72 cells/1.1 sq. feet, 50 cc/cell). Starter fertilizer was incorporated in all flats at a base rate of 16 lb N/acre as 18-24-6 to assure adequate growth. The seedlings were in the 2nd true leaf stage on January 3 when they were treated with fertilizer (18-24-6) at 96 lbs. N/acre and two rates of PP-333 (0.074 and 0.74 lbs./acre). On the 10th day of the test, January 13, height color, and fresh weight were recorded. The results are shown in Table IX.

TABLE IX

| Sample No. | Formulation | (lbs./acre) | | Percent of Control | | |
|---|---|---|---|---|---|---|
| | | N | PP-333 | Height | Color | Fresh Weight |
| 1 | Fertilizer | 96 | 0 | 93 | 209 | 115 |
| 2 | PGR | 0 | .074 | 75 | 212 | 91 |
| 3 | Fert. plus PGR | 96 | .074 | 67* | 265* | 98* |
| 4 | PGR | 0 | .74 | 61 | 229 | 72 |
| 5 | Fert. plus PGR | 96 | .74 | 54* | 287 | 72* |

*Synergistic response

As shown in Table IX, the combination of fertilizer and PGR resulted in a smaller plant (shorter and less fresh weight) with darker green foliage than when plants received fertilizer alone. The combination of fertilizer and PGR was more effective in affecting plant response than either material applied alone.

EXAMPLE 10

Burpless Slicing Cucumber seedlings in the 2-4 leaf stage were transplanted into Metro-Mix 200 and fertilized with Starter fertilizer at 87 or 261 lbs/N acre on May 22. On May 30, PP-333 was applied as a liquid drench using 125 ml of water containing 0, 0.1, 1.0 and 10.0 ppm of PP-333 (0, 0.006, 0.06 0.6 lbs/acre). On July 16, the plants were harvested and a number of observations recorded. These are set forth in Table X. The total male flowers were observed on the 24th day of the test, the total female flowers on the 47th day. (A reduction in male flowers with an increase in female flowers increases the potential for higher cucumber yield.)

TABLE X

| Sample | Formulation | lbs/acre N | lbs/acre PP-333 | Plant Ht. (cms) | Plant Color (10 > 1) | Plant Quality (1 > 10) | Plant Wt. (gms) | Internodes (No.) | Total Flowers Male (No.) | Total Flowers Female (No.) | Fruit Wt. (gms) | Tissue Analysis (% N) |
|---|---|---|---|---|---|---|---|---|---|---|---|---|
| 1 | Fertilizer | 87 | 0 | 298 | 2.0 | 5.5 | 170 | 25 | 61 | 12 | 566 | 0.62 |
| 2 | Fertilizer & PGR | 87 | .006 | 310 | 2.5 | 5.5 | 164 | 27 | 71 | 17 | 332 | 0.62 |
| 3 | Fertilizer & PGR | 87 | .06 | 108 | 6.5 | 3.5 | 145 | 20 | 65 | 31 | 121 | 0.66 |
| 4 | Fertilizer & PGR | 87 | .6 | 65 | 8.5 | 3.0 | 123 | 20 | 48 | 34 | 6 | 1.14 |
| 5 | Fertilizer | 261 | 0 | 420 | 2.5 | 5.0 | 278 | 33 | 53 | 18 | 689 | 0.54 |
| 6 | Fertilizer & PGR | 261 | .006 | 295 | 3.0 | 5.0 | 223 | 27 | 57 | 19 | 856 | 0.70 |
| 7 | Fertilizer & PGR | 261 | .06 | 97 | 7.0 | 2.5 | 163 | 21 | 57 | 23 | 591 | 0.78 |
| 8 | Fertilizer & PGR | 261 | .6 | 69 | 9.5 | 2.5 | 170 | 20 | 47 | 39 | 10 | 1.26 |

As shown in Table X, the addition of PP-333 to fertilized plants (87 or 261) lbs N/acre) improved plant color, quality, increased number of female flowers and percent nitrogen in the tissue with an associated decrease in male flowers and plant and fruit weight. It is of interest that the number of female flowers can be increased by 158% (12 vs 31 flowers) by combining fertilizer and PP-333 (87 and 0.06 lb/acre respectively). If the fertilizer level is tripled, the female flower count increases only 50% (12 vs 18 flowers). The lack of fruit set is associated with poor pollination in the greenhouse and is not due to treatment. The addition of PP-333 (0.06 lb/acre) to the low rate of nitrogen (87 lb N/acre) resulted in a dramatic increase in plant color and quality and female flowers with an associated compact habit of growth as compared to plants fertilized with triple the fertilizer level without PP-333 added (261 lbs N/acre). The higher rate as compared to the lower rate of fertilizer was more effective in increasing the biological activity of PP-333 in respect to plant color, quality weight, and internode length.

EXAMPLE 11

Royal Oak Leaf Lettuce was seeded in pure silica sand on April 30 and transplanted to 4" pots (400 cc) containing silica sand. On May 10, all plants were maintained on a 24 lbs N/acre applied in distilled water containing all essential elements (Hoagland solution). On June 4th, fertilizer and PGR were applied using 48 lbs. N/acre in a solution containing all other essential elements and 0.006 lbs. ai of PP-333/acre. On the 24th day of the test, the plants were harvested and observations were recorded as shown in Table XI. All plants, including the control, received a base rate of 24 lbs. of nitrate-nitrogen per acre to sustain growth. The control received no PGR. The total fresh weight, leaf N, and N removed was observed in 4 harvests on the 17th, 22nd, and 35th and 57th day of the test.

TABLE XI

| Sample No. | Formulation | (lbs./acre) N | (lbs./acre) PP-333 | Percent of Control Fresh Weight | Percent of Control Height | Percent of Control Color | Percent of Control Quality | Percent of Control Leaf N | Percent of Control Nitrogen Removed |
|---|---|---|---|---|---|---|---|---|---|
| 1 | Fertilizer | 48 | 0 | 124 | 107 | 114 | 103 | 103 | 128 |
| 2 | PGR | 0 | .006 | 97 | 103 | 107 | 103 | 110 | 106 |
| 3 | Fert. & PGR | 48 | .006 | 146* | 114* | 130* | 115* | 126* | 182* |

*Synergistic response

As shown in Table XI, the combination of fertilizer and PGR resulted in a greater response than either material applied alone. In contrast to other studies, PP-333 resulted in a synergistic stimulation of growth when combined with fertilizer.

EXAMPLE 12

Royal Oak Leaf Lettuce was seeded on June 12 in a 8/1 sand/loam placed in a 4" pot (400 cc volume). On June 18, the plants were thinned to 4/pot and supplemented with N, $P_2O_5$ and $K_2O$ (43.5, 174 and 43.5 lbs. per acre, respectively) to assure an adequate growth response. On June 25, nitrogen as methylene urea (38% CWIN) was applied at 87 lbs N/acre with and without PP-333 at 0.06 lb/acre. Observations were recorded periodically and are reported in Table XII. Color was recorded on the 22nd day of the test. The total fresh weight, leaf N, and N removed were recorded in 4 harvests on the 17th, 22nd, and 35th, and 57th day of the test.

TABLE XII

| Sample No. | Formulation | (lbs./acre) N | (lbs./acre) PP-333 | Percent of Control Color | Percent of Control Total F.W. | Percent of Control Leaf N | Percent of Control N Removed |
|---|---|---|---|---|---|---|---|
| 1 | Fertilizer | 87.5 | 0 | 185 | 173 | 135 | 197 |
| 2 | PGR | 0 | .06 | 111 | 90 | 115 | 94 |
| 3 | Fert. & PGR | 87.5 | .06 | 223* | 186* | 149 | 229* |

*Synergistic response

As shown in Table XII, the combination of fertilizer and PGR resulted in a greater response (color, total F.W., Leaf N and N-removed) then when either fertilizer or PP-333 were applied alone.

EXAMPLE 13

Great Lakes Head lettuce seedlings in the 2-4 leaf stage were transplanted into Metro Mix 200 and fertilized with Starter fertilizer at 87 or 261 lbs N/acre on May 22 and May 30. PP-333 was applied as a liquid drench using 125 ml of water containing 0, 0.1, 1.0, 10.0 ppm of PP-333 (0.006, 0.06 and 0.60 lbs/acre). On June 23, the plants were harvested and a number of observations recorded. These are shown in Table XIII.

TABLE XIII

| Sample | Formulation | lbs./acre N | PP-333 | Ht. (cms) | Width (cms) | Color (10 > 1) | Quality (1 > 10) | Fr. Wt. (gms) | Tissue (% N) |
|---|---|---|---|---|---|---|---|---|---|
| 1 | Fertilizer | 87 | 0 | 16 | 26 | 2.3 | 5.7 | 301 | 3.94 |
| 2 | Fertilizer & PGR | 87 | .006 | 22 | 38 | 4.3 | 2.7 | 306 | 3.71 |
| 3 | Fertilizer & PGR | 87 | .06 | 18 | 34 | 7.0 | 1.7 | 308 | 2.98 |
| 4 | Fertilizer & PGR | 87 | .60 | 12 | 34 | 9.0 | 4.0 | 216 | 4.19 |
| 5 | Fertilizer | 261 | 0 | 22 | 41 | 5.3 | 2.3 | 428 | 3.72 |
| 6 | Fertilizer & PGR | 261 | .006 | 22 | 39 | 5.3 | 2.7 | 386 | 4.89 |
| 7 | Fertilizer & PGR | 261 | .06 | 21 | 41 | 8.0 | 1.0 | 359 | 3.92 |
| 8 | Fertilizer & PGR | 261 | .60 | 12 | 36 | 10.0 | 4.3 | 237 | 5.21 |

As shown in Table XIII, the combination of low rates of nitrogen (87 lbs/acre) and low rates of PP-333 (0.006–0.06 lbs/acre) resulted in plants of color and quality approximately equal or superior to plants fertilized with 3 times as much nitrogen (261 lbs/acre) however, head weights were reduced by 30%. When compared at equal rates of nitrogen (87 lbs N/acre) the addition of 0.006–0.06 lbs PP-333/acre improved plant color and quality with a slight increase in head weights (2%).

At the higher rate of nitrogen, the addition of 0.006 lbs/acre of PP-333 did not improve plant color or quality, however, at 0.06 lbs/acre color and quality were dramatically improved, however, yields were reduced by 16%. The highest rate of PP-333 (0.6 lbs./acre) improved color and quality of the lettuce at the lowest rate of nitrogen. At the higher rate of nitrogen, color improved but quality declined as compared to equal rates of nitrogen without PP-333. Yields were also reduced by 30–45% as compared to plants fertilized with Starter Fertilizer only. When the proper rate of PP-333 is combined with Fertilizer, improved color and quality is realized with no loss in head weight. The higher rate as compared to the lower rate of fertilizer was more synergistic with PP-333 in respect to height, fresh weight, and tissue nitrogen.

In the following examples, 14–17, woody ornamentals (eg. Euonymus, Juniper, Thuja and Buxus) were treated with various rates of PP-333 in the presence of low and high rates of fertilizer. Foliage color, plant quality, height, width, shoot fresh weight and tissue analysis were recorded.

EXAMPLE 14

Metro Mix 300 is a trademark for a potting media which is the same as Metro Mix 200 but contains, in addition, composted pine bark.

Euonymus patens 'Pauli' potted liners (2-½" pot) were potted up in 1 gallon cans on May 17 containing a synthetic potting media (Metro Mix 300). The plants were fertilized with a sulfur coated urea fertilizer having a 20-4-10 analysis using 436 or 1307 lbs. N/acre and treated with 125 ml of water containing either 1 or 100 ppm of PP-333 (0.06 and 6.0 lbs./acre) on June 19. The plants were placed in a nursery and watered as needed to assure a minimum of one inch of water/week. On October 18, a number of observations were recorded and are shown in Table XIV.

TABLE XIV

| Sample | Formulation | lbs./acre N | PP-333 | Color (10 > 1) | Quality (1 > 10) | Height (cm) | Width (cm) | Total Length (cm) | Shoots F.W. (gms) | Tissue Analysis (% N) |
|---|---|---|---|---|---|---|---|---|---|---|
| 1 | Fertilizer | 436 | 0 | 3.9 | 5.5 | 36 | 52 | 241 | 49 | 1.10 |
| 2 | Fertilizer & PGR | 436 | .06 | 5.7 | 4.5 | 43 | 57 | 290 | 58 | 1.22 |
| 3 | Fertilizer & PGR | 436 | 6.0 | 6.4 | 4.0 | 34 | 40 | 167 | 49 | 1.50 |
| 4 | Fertilizer | 1307 | 0 | 7.2 | 2.7 | 49 | 65 | 393 | 82 | 1.60 |
| 5 | Fertilizer & PGR | 1307 | .06 | 8.8 | 2.3 | 52 | 59 | 328 | 80 | 1.92 |
| 6 | Fertilizer & PGR | 1307 | 6.0 | 10.0 | 1.9 | 30 | 39 | 146 | 58 | 2.31 |

The addition of PP-333 at the low rate (0.06 lb./acre) improved plant color and quality and increased the percent nitrogen in the tissue regardless of nitrogen level. However, at the low rate of nitrogen, growth was stimulated (height, width, total shoot length, and fresh weight), while it was retarded at the high rate of nitrogen (width, shoot length, and fresh weight), as compared to plants receiving fertilizer only. At the higher rate of PP-333 (6.0 lbs./acre) plant color and quality were improved, tissue N increased, and growth was retarded at both N levels (height, width, total shoot length, and fresh weight), as compared to plants receiving only fertilizer. These differences were more dramatic at the higher nitrogen level (exception: 6.0 lbs. PP-333/acre applied to plants fertilized with 436 lbs. N/acre had comparable fresh weight as those receiving fertilizer only. Total shoot length, however, was dramatically reduced suggesting more weight per shoot). Note that the low rate of nitrogen with the high rate of PP-333 (436 lbs. N and 6.0 lbs. PP-333/acre) exhibited a color, quality, and tissue analysis (% N) that was similar to plants receiving 3 times more nitrogen. In contrast to earlier findings, certain plants require higher rates of PP-333 to provide a desirable response with nitrogen. In this case, 6.0 lbs. of PP-333/acre were required. However, it has been reported (Barrett, J. E., 1982, Hort. Science 17 (6): 896–897) that media containing bark reduced the biological activity of PP-333.

EXAMPLE 15

Juniperus horizontalis plumosa 'Youngstown' potted liners (2-½" pots) were potted up in 1 gallon cans on May 17, containing a synthetic potting media (Metro-Mix 300). The pots were fertilized with sulfur coated urea (20-4-10) using 436 or 1307 lbs. N/acre and treated with either 1.0 or 100 ppm PP-333 contained in 125 ml of water (0.06, and 6.0 lbs./acre) on June 19. The plants were placed in a nursery and watered as needed to assure a minimum of one inch of water per week. On October 10, a number of observations were recorded and are shown in Table XV.

TABLE XV

| Sample | Formulation | lbs./acre N | PP-333 | Color (10 > 1) | Quality (1 > 10) | Height (cm) |
|---|---|---|---|---|---|---|
| 1 | Fertilizer | 436 | 0 | 4.4 | 4.4 | 31 |
| 2 | Fertilizer & PGR | 436 | .06 | 6.1 | 3.7 | 32 |
| 3 | Fertilizer & PGR | 436 | 6.0 | 4.4 | 3.9 | 28 |
| 4 | Fertilizer | 1307 | 0 | 6.5 | 2.5 | 32 |
| 5 | Fertilizer & PGR | 1307 | .06 | 7.2 | 2.4 | 33 |
| 6 | Fertilizer & PGR | 1307 | 6.0 | 7.2 | 3.0 | 27 |

The addition of PP-333 improved plant color and quality in most cases, with little effect on plant height, except at the highest rate of PP-333 (6.0 lbs./acre) where height was reduced slightly. It appears that narrow leaf evergreens are not very responsive to this PGR. However, the response realized (i.e. improved color and quality with only moderate effects on growth) are of economic significance. This lack of response at lower rates may be associated with the inactivation by the bark in the media.

EXAMPLE 16

Thuja occidentalis "Pyramid" potted liners (2½" pots) were potted up in 1 gallon cans on May 17, containing a synthetic potting media (Metro Mix 300). The pots were fertilized with sulfur-coated urea (20-4-10) using 436 and 1307 lbs. N/acre and treated with 125 ml of water containing 0, 1.0, or 100 ppm of PP-333 (0, 0.06 and 6.0 lbs./acre) on June 19. The plants were placed in a nursery and watered as needed to assure a minimum of one inch of water/week. On May 22, a number of observations were recorded and are shown in Table XVI.

TABLE XVI

| Sample | Formulation | (lbs./acre) N | PP-333 | Color (10 > 1) | Quality (1 > 10) | Ht. (CMS) | Width (CMS) | Foliage Density (10 > 1) | Top F.W. (GMS) | Tissue Analysis (%) |
|---|---|---|---|---|---|---|---|---|---|---|
| 1. | Fertilizer only | 436 | 0 | 8.3 | 3.8 | 46.3 | 20.6 | 6.0 | 75.7 | 1.80 |
| 2. | Fertilizer & PGR | 436 | 0.06 | 7.2 | 2.5 | 47.9 | 20.7 | 6.3 | 85.2 | 1.67 |
| 3. | Fertilizer & PGR | 436 | 6.00 | 8.3 | 3.4 | 48.2 | 19.8 | 5.7 | 74.1 | 1.80 |
| 4. | Fertilizer Only | 1307 | 0 | 8.8 | 3.1 | 41.8 | 20.4 | 7.0 | 95.1 | 1.96 |
| 5. | Fertilizer & PGR | 1307 | 0.06 | 9.0 | 2.6 | 44.1 | 23.0 | 7.7 | 127.4 | 2.10 |
| 6. | Fertilizer & PGR | 1307 | 6.00 | 9.7 | 2.3 | 49.6 | 26.5 | 9.7 | 151.8 | 2.26 |

At the low rate of nitrogen, PP-333 had little or no effect on plant growth (color, quality, height, width, foliage density, top fresh weight and tissue nitrogen). In contrast, at the higher rate of nitrogen the presence of PP-333 improved plant color, quality, height, width, foliage density, top fresh weight and tissue analysis. In contrast to other plants tested, this variety is stimulated by PP-333 but only in the presence of adequate nutrition. These observations again, demonstrate the importance of N/PP-333 balance and rate to assure a synergistic response.

EXAMPLE 17

Buxus microphylla Koreana potted liners (2-½" pots) were potted up in a synthetic potting media (Metro Mix 300) and fertilized with 2439 lbs. N/acre as a 14-3-3 (% N, $P_2O_5$ and $K_2O$) containing 2.1% water soluble nitrogen. The plants were contained in 1 gallon cans and irrigated as needed to assure a minimum of 1 inch of water/week. The fertilizer was surface applied, followed by the PGR, using 125 ml. of water containing 25 ppm of PP-333 (1.5 lb./acre). On October 18, a number of observations were recorded and are shown in Table XVII. As in other examples, the control received neither fertilizer nor PGR.

TABLE XVII

| | | lbs./acre | | Percent of Control | | | | | | |
|---|---|---|---|---|---|---|---|---|---|---|
| | | | | Plant | | | | Shoot | | |
| Sample | Formulation | N | PP-333 | Height | Width | Color | Quality | Total Length | F.W. | Nitrogen |
| 1 | Fertilizer | 2439 | 0 | 150 | 207 | 221 | 170 | 271 | 361 | 147 |
| 2 | Plant Growth Reg | 0 | 1.5 | 83 | 87 | 91 | 106 | 88 | 115 | 98 |
| 3 | Fertilizer & PGR | 2439 | 1.5 | 121* | 153* | 251* | 176 | 171* | 246* | 165* |

*Synergistic response

The addition of PP-333 in the absence of fertilizer had very little impact on plant response. However, when combined with fertilizer, a synergistic response was realized. The plant height, width, total shoot length, and fresh weight were reduced as compared to plants receiving fertilizer only. In contrast, leaf color and the nitrogen increased in the plant tissue. The higher rate of PP-333 required to realize biological activity may be associated with the inactivations of PP-333 by the bark in the potting media. The addition of PP-333 to fertilized plants resulted in shorter, more compact plants which were darker green and exhibited comparable plant quality to plants receiving fertilizer alone.

The precise ranges of fertilizer and growth regulator, as well as the precise ratios of nitrogen to plant growth regulator, vary depending upon the type of plant treated, the type of fertilizer used and its mode of application. However, these ranges will all fall within the general ranges of overall proportions and amounts set forth in the claims which follow. The fertilizer may be any nitrogen fertilizer of the type used on plants, vegetables, and crops including both fast and slow release granular and liquid formulations. Examples of useful slow release granular nitrogen fertilizer formulations are set forth in U.S. Pat. Nos. 3,705,794 to Czurak et al., 4,025,329 to Goertz, and 4,378,238 to Goertz. As set forth in these patents, the fertilizers may be accompanied by nutrients and micronutrients in addition to nitrogen and by other active ingredients, the latter including herbicides, fungicides and other pesticides.

We claim:

1. A process for treating vegetation comprising herbaceous and woody ornamental plants and vegetable crops comprising applying to the vegetation a nitrogen containing fertilizer and from 0.006 to 6.0 pounds per acre of a plant growth regulator, said plant growth regulator selected from the group consisting of paclobutrazol and flurprimidol being a compound which regulates the growth of said vegetation by retardation of gibberellin synthesis, the ratio by weight of nitrogen in said fertilizer to said plant growth regulator being at least forty to one, said fertilizer and plant growth regulator being applied in proportions which are effective to improve the quality of the vegetation, the improvement in quality being both greater and extending for a longer period than that resulting from the application of the fertilizer or plant growth regulator alone.

2. The process of claim 1 in which the plant growth regulator is paclobutrazol.

3. The process of claim 1 in which the plant growth regulator is flurprimidol.

4. The process of claim 1 in which the fertilizer and plant growth regulator are applied to the vegetation as a granular composition in a single application.

5. The process of claim 1 in which the fertilizer and plant growth regulator are applied to the vegetation as a liquid composition in a single application.

6. The process of claim 1 in which the fertilizer is a fast release fertilizer.

7. The process of claim 6 in which the fast release fertilizer is urea.

8. The process of claim 1 in which the fertilizer is a slow release fertilizer.

9. The process of claim 8 in which the fertilizer is sulfur coated urea.

10. The process of claim 8 in which the fertilizer is methylene urea.

11. The process of claim 1 in which the ratio by weight of nitrogen in said fertilizer to said plant growth regulator is at least 100 to one.

12. The process of claim 1 in which the vegetation is woody ornamental plants.

13. The process of claim 12 in which the plant growth regulator is applied in an amount of 0.06 to 6.0 pounds per acre.

14. The process of claim 12 in which the fertilizer is applied in an amount of from 400 to 2500 pounds of nitrogen per acre.

15. The process of claim 1 in which the vegetation is herbaceous ornamental plants and vegetable crops.

16. The process of claim 15 in which the plant growth regulator is applied in an amount of 0.006 to 0.74 pounds per acre.

17. The process of claim 15 in which the fertilizer is applied in an amount of from 40 to 400 pounds of nitrogen per acre.

18. The process of claim 1 in which the fertilizer and plant growth regulator are applied separately, the fertilizer being applied before damage to the vegetation by the plant growth regulator.

19. A composition for treating vegetation comprising herbaceous and woody ornamental plants and vegetable crops comprising a nitrogen containing fertilizer and from 0.006 to 6.0 pounds of a plant growth regulator selected from the group consisting of paclobutrazol and flurprimidol, said amount being based on an amount of the composition for treating one acre of said vegetation, said plant growth regulator being a compound which regulates the growth of said vegetation by retardation of gibberellin synthesis, the ratio by weight of nitrogen in said fertilizer to said plant growth regulator being at least forty to one, said fertilizer and plant growth regulator being present in said composition in a proportion which is effective when applied to said vegetation to improve the quality of the vegetation, the improvement in quality being both greater and extending for a longer period than that resulting from the application of the fertilizer or plant growth regulator alone.

20. The composition of claim 18 in which the plant growth regulator is paclobutrazol.

21. The composition of claim 18 in which the plant growth regulator is flurprimidol.

22. The composition of claim 17 in which the composition is a granular formulation.

23. The composition of claim 19 in which the composition is a liquid formulation.

24. The composition of claim 19 in which the fertilizer is a fast release fertilizer.

25. The composition of claim 24 in which the fast release fertilizer is urea.

26. The composition of claim 19 in which the fertilizer is a slow release fertilizer.

27. The composition of claim 26 in which the fertilizer is sulfur coated urea.

28. The composition of claim 26 in which the fertilizer is methylene urea.

29. A composition for treating vegetation comprising herbaceous ornamental plants and vegetable crops comprising a nitrogen containing fertilizer and from 0.006 to 0.60 pounds of a plant growth regulator selected from the group consisting of paclobutrazol and flurprimidol, said amount being based on an amount of the composition for treating one acre of said vegetation, said plant growth regulator being a compound which regulates the growth of said vegetation by retardation of gibberellin synthesis, the ratio by weight of nitrogen in said fertilizer to said plant growth regulator being at least one hundred to one, said fertilizer and plant growth regulator being present in said composition in a proportion which is effective when applied to said vegetation to improve the quality of the vegetation, the improvement in quality being both greater and extending for a longer period than that resulting from the application of the fertilizer or plant growth-regulator alone.

30. A composition for treating vegetation comprising woody ornamental plants comprising a nitrogen containing fertilizer and from 0.060 to 6.0 pounds of plant growth regulator selected from the group consisting of paclobutrazol and flurprimidol, said amount being based on an amount of the composition for treating one acre of said vegetation, said plant growth regulator being a compound which regulates the growth of said vegetation by retardation of gibberellin synthesis, the ratio by weight of nitrogen in said fertilizer to said plant growth regulator being at least seventy to one, said fertilizer and plant growth regulator being present in said composition in a proportion which is effective when applied to said vegetation to improve the quality of the vegetation, the improvement in quality being both greater and extending for a longer period than that resulting from the application of the fertilizer or plant growth regulator alone.

* * * * *